United States Patent [19]

Bonne et al.

[11] Patent Number: 4,958,076

[45] Date of Patent: Sep. 18, 1990

[54] SELECTIVE NATURAL GAS DETECTING APPARATUS

[75] Inventors: Ulrich Bonne, Hopkins; Robert J. Matthys, Minneapolis, both of Minn.

[73] Assignee: Gas Research Institute, Chicago, Ill.

[21] Appl. No.: 308,469

[22] Filed: Feb. 10, 1989

[51] Int. Cl.$^5$ ............................................. G01N 21/61
[52] U.S. Cl. ...................................... 250/343; 250/339
[58] Field of Search ............. 250/343, 339, 345, 338.5

[56] References Cited

U.S. PATENT DOCUMENTS

| | | | |
|---|---|---|---|
| 2,741,703 | 4/1956 | Munday. | |
| 3,551,678 | 12/1970 | Mitchell. | |
| 3,678,262 | 7/1972 | Hermann. | |
| 3,743,426 | 7/1973 | Steinberg | 250/345 |
| 3,790,797 | 2/1974 | Sternberg et al. | 250/345 |
| 3,832,548 | 8/1974 | Wallack | 250/343 |
| 3,893,770 | 7/1975 | Takami et al. | 250/343 |
| 3,897,194 | 7/1975 | Hawes | 250/345 |
| 3,968,367 | 7/1976 | Berg | 250/339 |
| 4,054,384 | 10/1977 | Hawes | 250/345 |
| 4,273,450 | 6/1981 | Watanabe et al. | 250/345 |
| 4,297,579 | 10/1981 | Spaeth | 250/343 |
| 4,507,558 | 3/1985 | Bonne | 250/343 |
| 4,520,265 | 5/1985 | Griggs et al. | 250/339 |
| 4,543,481 | 9/1985 | Zwick | 250/338.5 |
| 4,567,366 | 1/1986 | Shinohara | 250/343 |

FOREIGN PATENT DOCUMENTS 1000070 11/1976 Canada .................. 250/343

Primary Examiner—Carolyn E. Fields
Attorney, Agent, or Firm—Thomas W. Speckman; Douglas H. Pauley

[57] ABSTRACT

A selective gas detecting apparatus for determining the concentration and type of hydrocarbon gas in a gas sample based upon absorption of infrared radiation by the gas sample, the apparatus having at least two infrared radiation absorption channels with the wavelengths for measurement in the two channels selected as 3.2 microns and 3.4 microns, signals in the two channels being processed to formulate an indication of absorbance of hydrocarbons at the selected wavelength, the absorbance signal in one channel being displayed as an indication of concentration of approximately the total hydrocarbon gas in air and the ratio of absorbances being displayed as an indication of the type of hydrocarbon in air and independent of the concentration of the gas.

19 Claims, 2 Drawing Sheets

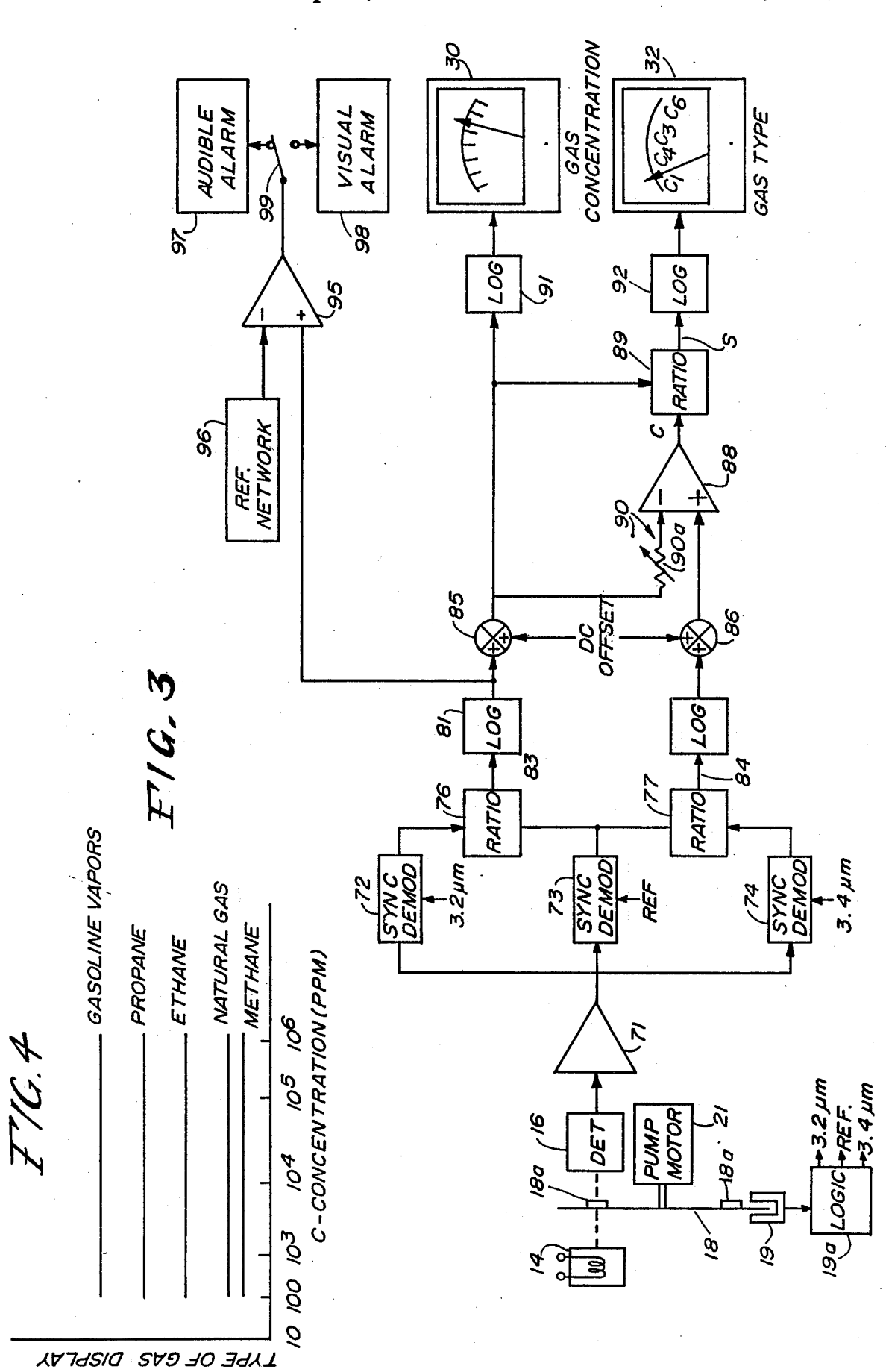

SELECTIVE NATURAL GAS DETECTING APPARATUS

BACKGROUND OF THE INVENTION

This invention relates to gas detecting apparatus, and more particularly, to natural gas detecting apparatus of the type which operate on the basis of absorption of infrared light.

Utilities which distribute natural gas require reliable, portable gas-leak detectors for use in maintenance of gas supply lines. Existing natural gas detectors are either costly, sensitive and non-selective or low cost, insensitive and non-selective. Non-selective gas detectors respond to any combustible gas. Selective gas detectors are specific to hydrocarbon gases. The two presently most used detectors are based on hydrogen flame ionization and on hot wire catalysis, cannot distinguish among different types of hydrocarbons. However, it is necessary to distinguish among different types of hydrocarbons in order to distinguish a pipeline gas from gasoline vapors or sewer or swamp gas and so reduce leak surveyor time wasted on false alarms. Ethane content, if measurable, provides a good means to discriminate between pipeline gas and interfering sewer or swamp gases because the latter contain practically no ethane, while pipeline gas does, in varying degrees. Gasoline vapors and propane (LP gas) can also generate a false alarm with conventional instruments. However, their infrared absorption is shifted relative to that of methane, as will be described later, as it is the basis for this invention to eliminate sending false alarms.

In U.S. Pat. No. 4,507,558, there is disclosed a selective detector for natural gas which discriminates between low concentrations of natural gas and other methane sources by measuring the characteristics of the methane/ethane ratio of natural gas as well as by using a combustible gas sensor. The operation of this detector is based on infrared light absorption of methane and ethane in combination with another non-specific combustible gas detector whereby the detector has the ability to detect non-specifically, the presence of a combustible gas, and to define the nature of the combustible gas. Thus, this natural gas detector utilizes two types of detection including nondispersive infrared detectors and a non-specific combustible detector such as hot-wire catalytic combustible detector. The detector determines concentration of both methane or ethane irrespective of the concentration of the other gas by using absorption cells placed in front of the detectors. The detector includes a light emitting diode which issues light centered around 3.32 microns and a reference light source which emits light at a wavelength outside of this band. Although this arrangement permits distinguishing among different types of hydrocarbons, the requirement for a hotwire catalytic combustible detector adds cost and complexity to the device and increases power consumption.

It would be desirable to have a natural gas detector which can distinguish among different types of hydrocarbons, and which provides information to the user on the amount and type of combustible gases in the environment.

SUMMARY OF THE INVENTION

It is an object of the invention to provide an improved natural gas detector.

Another object of the invention is to provide a natural gas detector which can distinguish among different types of hydrocarbons.

Another object of the invention is to provide a natural gas detector which provides information to the user on the amount and type of combustible gases in the environment.

A further object of the invention is to provide a natural gas detector which is characterized by simplicity, greater response time and low cost than known discriminating natural gas detectors.

A further object of the invention is to provide a natural gas detector having the ability to recognize propane leaks, or gasoline vapors or swamp or sewer gas.

A further object of the invention is to provide a natural gas detector which provides detection over the entire range of combustible gas without requirement for range switching for its display unit.

These and other objects are achieved by the present invention which has provided a selective gas detecting apparatus for determining the concentration and type or average type of hydrocarbon gas in a gas sample based upon absorption of infrared radiation by the gas sample. The gas detecting apparatus comprises means for passing infrared radiation through the gas sample, infrared radiation detecting means for detecting infrared radiation passed through the gas sample and producing in a first signal channel a first measurement signal indicative of a first wavelength absorbed by the gas sample, and producing in a second signal channel a second measurement signal indicative of a second wavelength absorbed by the gas sample, processing circuit means including first circuit means responsive to said first measurement signal for providing a first output signal corresponding to a first total concentration of hydrocarbons in the gas sample, second circuit means responsive to said second measurement signal for providing a second output signal corresponding to a second total concentration of hydrocarbons in the gas sample, first function generating circuit means for receiving said first output signal and providing a first absorbance signal corresponding to the natural logarithm of said first output signal and indicative of absorbance by said gas sample of infrared radiation at said first wavelength, second function generating circuit means for receiving said second output signal and providing a second absorbance signal corresponding to the natural logarithm of said second output signal and indicative of absorbance by said gas sample of infrared radiation at said second wavelength, ratio determining means responsive to said first and second absorbance signals for providing a ratio signal corresponding to the ratio of said first and second absorbance signals, said ratio signal being indicative of the type or average type of hydrocarbon in the gas sample, and display means responsive to said first absorbance signal and said ratio signal for providing an indication of the concentration and type or average type of hydrocarbon gas in the gas sample, respectively.

All working or main absorption channels use the infrared absorption of light energy by the carbon-hydrogen bonds in hydrocarbons, which shift in intensity in characteristic ways as the structure or chain length of the hydrocarbon changes. These shifts occur within about 3.0 to 3.8 microns for the fundamental C-H excitation and around 1.6 microns for the first harmonic excitation.

The invention consists of certain novel features and structural details hereinafter fully described, illustrated in the accompanying drawings, and particularly pointed out in the appended claims, it being understood that various changes in the details may be made without departing from the spirit, or sacrificing any of the advantages of the present invention.

DESCRIPTION OF THE DRAWINGS

For the purpose of facilitating and understanding the invention, there is illustrated in the accompanying drawings a preferred embodiment thereof, from an inspection of which, when considered in connection with the following description, the invention, its construction and operation, and many of its advantages will be readily understood and appreciated.

FIG. 3 is a block diagram of the natural gas detector provided by the present invention; and FIG. 4 is a graphical representation of the type of gas display of the detector versus individual gas concentrations.

DESCRIPTION OF A PREFERRED EMBODIMENT

Figure 1:
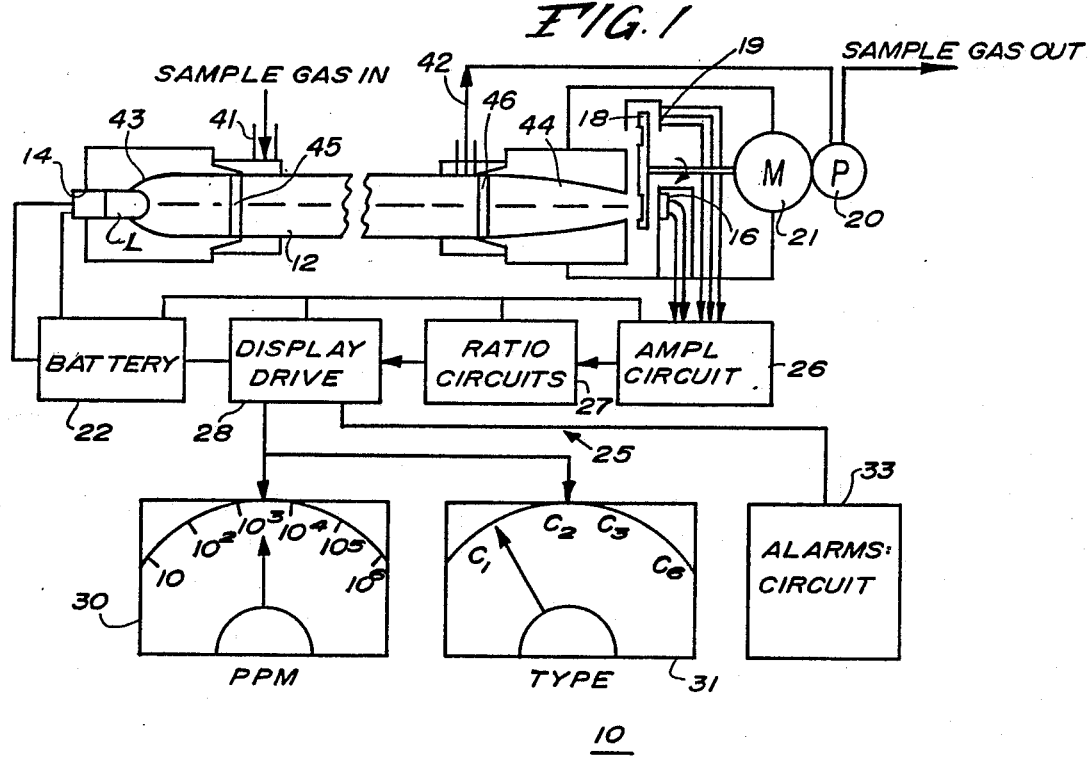
FIG. 1 is a simplified representation of the natural gas detector provided by the present invention.

Referring to FIG. 1, the operation of the natural gas detecting apparatus 10 provided by the present invention is based upon the absorption of infrared energy by a gas sample as the gas sample is pumped through a gas sample chamber defined by an optical cell 12. The natural gas detector 10 includes a gas detection arrangement which determines gas concentration, i.e. the total concentration of hydrocarbons in the gas sample, and the gas type, i.e. swamp or sewer gas, natural gas, propane, gasoline vapors and others. The gas sample is analyzed using optical cell 12 which defines a gas sample optical path length, an infrared radiation source 14 and an infrared radiation detector 16 with a rotatable chopper wheel 18 interposed therebetween. A pump 20 moves the sample gas through the optical cell 12 at the rate of about two liters per minute. The pump 20 is driven by a motor 21 which also drives the chopper wheel 18. The use of a common motor 21 to drive the chopper wheel 18 and the pump 20 reduces power requirements for the natural gas detector 10. The gas detecting apparatus 10 is energized from a battery 22 which may comprise a 12 volt (or two five volt) rechargeable nickel cadmium battery providing power for long hours of operation. The gas detecting apparatus consumes only four watts including the one watt pump 20.

The infrared radiation detector 16 detects infrared radiation in selected bands and produces electrical measurement signals at the wavelengths absorbed by the gases in the sample, and thus indicative of the gases which comprise the sample. Timing signals for use in processing the measurement signals are generated by a non-contacting type pickup 19 which may be an optical, magnetic or capacitive type device.

The signals produced by the detector 16 and the pickup 19 are applied to processing circuits indicated generally at 25. The processing circuits 25 include an amplifier and demodulating circuit 26, ratio circuits 27, and a display drive circuit 28 which provides drive signals for a pair of analog meters 30 and 32. An alarm circuit 33 provides an alarm indication whenever a preselected gas concentration level is reached or exceeded.

In accordance with one aspect of the invention, the natural gas detector uses selection of two infrared wavelengths 3.2 microns and 3.4 microns to determine concentration and type of hydrocarbon gas. Gas concentration is processed and displayed in terms of absorbance to minimize error. A representation of gas concentration is displayed by meter 30. To provide an indication of gas type, the processing circuits 25 of the gas detecting apparatus 10 compute the ratio of absorbances to obtain a signal indicative of the type of hydrocarbon gas in air and which is independent of gas concentration. This information is displayed by meter 32.

Considering the gas detector 10 in more detail, the optical cell 12 is about 25–100 centimeters in length and preferably 50 cm. The inner surface of the optical cell has a coating of gold to internally reflect the radiation directed thereto. The optical cell receives a sample of a gas to be analyzed via the suction action of the pump 20 which draws the gas sample into the optical cell through an inlet 41 and exhausts the gas sample from the optical cell 12 through an outlet 42. The light from the infrared radiation source is optically collimated by a reflector 43, channeled through the internally reflecting optical cell 12 and is concentrated by a parabolic, non-imaging concentrator 44 located forward of the detector 16. The optical cell 12 has windows 45 and 46 on each end which are sealed to the parabolic surfaces of the reflectors 43 and 44. The gas sample is applied to the optical cell 12 by a detector sample wand (not shown) which is attached to the inlet 41 of the optical cell. A suitable outlet hose (not shown) is connected between the outlet 42 and the pump 20.

The infrared radiation source 14 comprises a tungsten sub-miniature light bulb. To increase sensitivity, the output of the light source is mechanically chopped at a 50 to 1000 Hz (preferably 300) rate by the action of the chopper wheel 18.

Referring to FIGS. 1 and 3, the chopper wheel 18 is driven by the same motor 21 which operates the pump 20. The chopper wheel, may for example, comprise a one inch diameter disc with the separation between the optical axis and the chopper wheel axis being one-quarter inches in one embodiment. The chopper wheel 18 carries a plurality of narrow band interference filters 18a including filters at the two wavelengths 3.2 microns and 3.4 microns, and a reference wavelength which may be 2.9 or 3.9 microns, which only provide passage of infrared radiation at wavelengths 3.2 microns, 3.4 microns and 2.9 (or 3.9) microns to the infrared radiation detector 16. The non-contacting pickup 19 generates gating or phase timing signals for these three channels for demodulating the detection signals.

The signal output of the detector 16 is applied to the amplifier and demodulator circuit 26, the output of which is processed by ratio circuit 27 to obtain signals representative of absorbance and of the ratio of absorbances. These signals are applied to display drive circuit 28. The use of logarithmic values for purposes of display results in compression of the displayed information, obviating the need for range switching of the analog display meters.

Referring to FIG. 3, which illustrates the natural gas detecting apparatus 10 in simplified form, with the gas sample chamber omitted, signals detected by the detector 16 are applied to the input of the amplifier and demodulator circuit 26 which includes a buffer amplifier 71 and sync demodulator circuits 72-74. The output of amplifier 71 is commonly connected to the inputs of the demodulator circuits 72-74. The sync demodulator circuits 72, 73 and 74 have reference inputs which receive the phase reference signals generated by the pickup 19 and associated logic 19a. The chopper wheel produces an operating rate of 300 Hz for the detector. The sync demodulator circuits 72, 73 and 74 provide detector output signals indicative of the detection of wavelengths of 3.2 microns, 2.9 microns (or 3.9 microns), and 3.4 microns, respectively, each $\pm$ 0.1 microns. The signal outputs of sync demodulator are applied to the ratio circuits 27.

The ratio circuits 27 include a function generating circuit 76, a function generating circuit 77 and logarithm circuits 81 and 82. The ratio circuits 27 define two signal channels 83 and 84 for producing measurement signals corresponding to wavelengths at 3.2 microns and 3.4 microns, respectively, each indicative of a total concentration of hydrocarbons in the gas sample. A DC offset signal may be introduced into each of the signal channels by summing circuits 85 and 86.

Function generating circuit 76 provides a signal corresponding to the quotient of detector signal at 3.2 microns and the reference signal at 2.9 microns (or 3.9 microns). Function generating circuit 77 provides a signal corresponding to the quotient of detector signal at 3.4 microns and the reference signal at 2.9 microns (or 3.9 microns). The signal output provided by function generating circuit 76 is applied to logarithm circuit 81 which generates a signal corresponding to the natural log of its input signal. Similarly, the log of the signal provided by function generating circuit 77 is obtained by log circuit 82.

The signal channel at a wavelength near 3.2 microns measures the transmission: (1) $I/I_o = \exp(-kpC) = \exp(-x)$ where $I_o$ is intensity without hydrocarbons in the optical path, $I$ is intensity with hydrocarbons in the optical path, $(I-I_o)/I_o$ equals absorption, $k$ is the absorption coefficient, $x$ is absorbance, $p$ is the optical path length in centimeters and $C$ is concentration in parts per million (ppm).

Thus, the signals produced by logarithm circuits 81 and 82 represent absorbances. Absorbances are formulated and processed in signal channels 83 and 84 to minimize drifts at low concentrations and to maximize linearty at high concentrations.

The use of 3.2 microns and 3.4 microns provides a balance between discrimination among different hydrocarbons and commonality among them such that the total concentration of hydrocarbons is obtained from channel 83 and channel 84 is used to determine the type of hydrocarbon by obtaining the ratio of the signal in channel 84 relative to the signal in channel 83. Thus, the signal conducted in signal channel 83 represents the gas concentration. Signal channel 84 further includes a subtractor circuit 88, a function generating circuit 89 and an offset network 90 including variable resistance 90a which defines an offset factor 1/K1. In one embodiment, the value of the offset factor 1/K1 was 0.37. In signal channel 84, the signal conducted in signal channel 83 is applied through resistance 90a to the inverting input of subtractor circuit 88 which receives the signal in channel 84 at its non-inverting input. The signal output of the subtractor circuit 88 is applied to function generating circuit 89 which provides an output signal S which corresponds to the quotient of the signals in channels 84 and 83 and represents the type of hydrocarbon gas present in the sample gas.

Computation of the ratio of absorbances by function generating circuit 89 produces a signal which is indicative of the type or average type of hydrocarbon gas in air and largely independent of the concentration of the gas, as indicated by FIG. 4.

The absorbance signal in channel 83 is applied to logarithm circuit 91 which produces a drive signal for meter 30. Similarly the signal S representing the ratio of absorbances produced by function circuit 89 is applied to logarithm circuit 92 which produces a drive circuit for meter 32. Use of logarithmic values of the signals compresses the drive signals for the meters 30 and 32 and obviates the need for range switching. Very small values for the signal S indicate the presence primarily of methane. The value of offset factor K1 is chosen to make the signal S approximately equal to zero for methane. A small addition of higher hydrocarbons (C2 to C6 or higher) increases the measured value of signal S because of the shift in absorption of these hydrocarbons towards longer wavelengths. A small scale reading at C1 is indicative of swamp gas. A near mid-scale reading near C1 but between it and C2 is indicative of natural gas. A reading at C3 above mid scale is indicative of propane. A near full scale reading at C6 is indicative of gasoline vapors.

Figure 2:
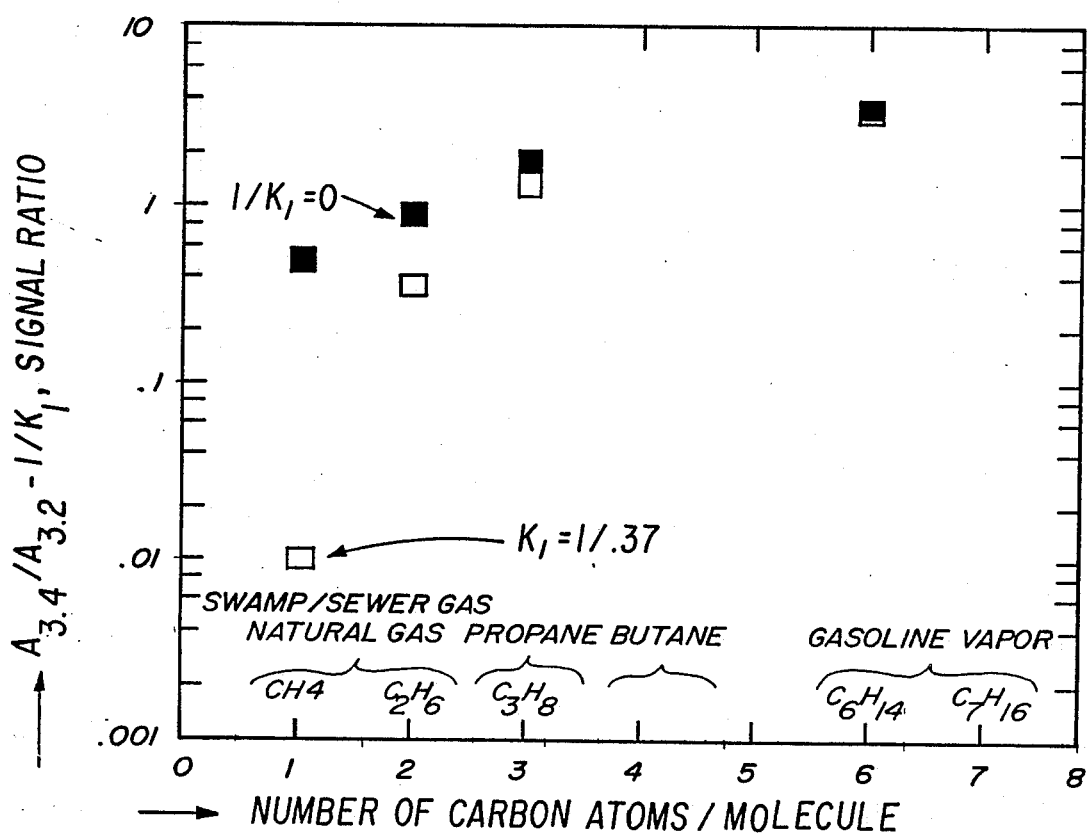
FIG. 2 is a graphic representation of the relationship between the signal output of the type or average type of the gas detector display versus different but individual types of hydrocarbons in a gas sample.

The gas detecting apparatus 10 measures the entire concentration range of methane from 10 to $10^6$ ppm and displays the result without range switching of the meters 30 and 32. FIG. 2 illustrates the results of measuring the signal S as the concentration shifted from methane to hexane and the number of carbon atoms per molecule increases from one to six, for an offset factor equal to zero, and for an offset factor equal to 0.37. The graph of FIG. 4 illustrates that signals obtained in signal channel 84 corresponds to the type of gas, rather than quantity or concentration of gas.

The alarm circuit includes a comparator circuit 95 which compares the amplitude of the signal in channel 83 with a reference value established by reference network 96 and energizes an audible alarm device 97 or a visual alarm device 98 as a function of the setting of a manually operated switch 99. The alarm circuit 33 provides an audible or visual alarm whenever the measured concentration in parts per million (ppm) surpasses an adjustable upper limit established by the reference network. This allows the user to concentrate on the sample collecting process rather than having to watch the meters 30 and 32 continuously.

We claim:

1. A selective gas detecting apparatus for determining a concentration and type or average type of hydrocarbon gas in a gas sample based upon absorption of infrared radiation by the gas sample, comprising: sampling means for passing infrared radiation through the gas sample, infrared radiation detecting means for detecting infrared radiation passed through the gas sample and producing in a first signal channel a first measurement signal indicative of a first wavelength absorbed by the gas sample, and producing in a second signal channel a second measurement signal indicative of a second wavelength absorbed by the gas sample, processing circuit means including first circuit means responsive to said first measurement signal for providing a first output signal corresponding to an indication of a first total concentration of hydrocarbons in the gas sample, second circuit means responsive to said second measurement signal for providing a second output signal corresponding to an indication of a second total concentration of hydrocarbons in the gas sample, first function generating circuit means for receiving said first output signal and providing a first absorbance signal corresponding to a natural logarithm of said first output signal and indicative of absorbance by said gas sample of infrared radiation at said first wavelength, second function generating circuit means for receiving said second output signal and providing a second absorbance signal corresponding to the natural logarithm of said second output signal and indicative of absorbance by the gas sample of infrared radiation at said second wavelength, ratio determining means responsive to said first and second absorbance signals for providing a ratio signal corresponding to the ratio of said first and second absorbance signals, said ratio signal being indicative of the type or average type of hydrocarbon in the gas sample, and display means responsive to said first absorbance signal and said ratio signal for providing and indication of the concentration and type or average type of hydrocarbon gas in the gas sample, respectively.

2. A gas detecting apparatus according to claim 1, wherein said first wavelength is 3.2 ±0.1 microns and said second wavelength is 3.4 ±0.1 microns.

3. A gas detecting apparatus according to claim 2, wherein said infrared radiation detecting means produces a reference measurement signal indicative of a third wavelength absorbed by the gas sample, said reference measurement signal being applied to said first and second circuit means for generating said first and second output signals.

4. A gas detecting apparatus according to claim 3, wherein said third wavelength is 2.9 ±0.1 microns.

5. A gas detecting apparatus according to claim 3, wherein said third wavelength is 3.9 ±0.1 microns.

6. A gas detecting apparatus according to claim 3, wherein said processing circuit means further comprises offset means for adjusting said ratio signal to be a preselected value when said ratio signal indicates that the type of hydrocarbon is methane.

7. A gas detecting apparatus according to claim 6, wherein said offset means includes means for producing an offset signal and circuit means for subtracting said offset signal from said first absorbance signal at the input of said ratio determining means.

8. A gas detecting apparatus according to claim 3, wherein said display means comprises first and second analog meters and third and fourth function generating circuit means, said third function generating circuit means being interposed between said ratio determining means and said first meter and responsive to said ratio signal for providing a signal corresponding to the logarithm of said ratio signal for driving said first meter, and said fourth function generating circuit means being interposed between said first function generation means and said second meter and responsive to said second absorbance signal for providing a signal corresponding to the logarithm of said second absorbance signal for driving said second meter.

9. A gas detecting apparatus according to claim 3, further comprising alarm means responsive to said second absorbance signal for providing an indication whenever a measured concentration exceeds a preselected level.

10. A gas detecting apparatus according to claim 3, wherein said ratio determining means comprises a function circuit providing a signal output corresponding to a quotient of said first and second output signals.

11. A gas detecting apparatus according to claim 4, wherein said infrared radiation detecting means comprises a single infrared detector, a chopper disc member bearing narrow band interference filter means interposed between an infrared source and said detector and rotatably mounted to present passage in sequence of infrared radiation at 3.4 microns, 3.2 microns, and 2.9 microns to said detector, pickup means for generating a plurality of reference signals in sequence with the interference of passage of infrared radiation in said related bands to said detector, first demodulating circuit means responsive to signal outputs of said detector and to a first one of said reference signals to produce said first measurement signal, and second demodulating circuit means responsive to said signal outputs of said detector and to a second one of said reference signals for producing said second measurement signal.

12. A gas detecting apparatus according to claim 11, wherein said gas sampling means includes means defining a gas sample chamber having a fluid inlet and a fluid outlet, a fluid pump means for moving the gas sample through said sample chamber and drive means for driving said pump means, said drive means being coupled to said disc member for rotating said disc member.

13. A selective gas detecting apparatus for determining a concentration and type or average type of hydrocarbon gas in a gas sample based upon absorption of infrared radiation by the gas sample comprising: means for passing infrared radiation from a source of infrared radiation through the gas sample, infrared detecting means for detecting infrared radiation passed through the gas sample including a single infrared detector and filter means interposed between said source of infrared radiation for producing a first detection signal indicative of a first wavelength absorbed by the gas sample, a second detection signal indicative of a second wavelength absorbed by the gas sample, and a reference signal indicative of a third wavelength absorbed by the gas sample, first demodulating circuit means responsive to detection signals provided by said detector and to said reference signal to produce a first measurement signal indicative of said first wavelength absorbed by the gas sample, second demodulating circuit means responsive to detection signals provided by said detector and to said reference signal to produce a second measurement signal indicative of said second wavelength absorbed by the gas sample, processing circuit means including first circuit means responsive to said first measurement signal for providing a first output signal corresponding to a first total concentration of hydrocarbons in the gas sample, second circuit means responsive to said second measurement signal for providing a second output signal corresponding to a second total concentration of hydrocarbons in the gas sample, first function generating circuit means for receiving said first output signal and providing a first absorbance signal corresponding to the natural logarithm of the first output signal and indicative of absorption by said gas sample of infrared radiation at said first wavelength, second function generating circuit means for receiving said second output signal and providing a second absorbance signal corresponding to the natural logarithm of said second output signal and indicative of absorption by said gas sample of infrared radiation at said second wavelength, ratio determining means responsive to said first and second absorbance signals for providing a ratio signal corresponding to the ratio of said first and second absorbance signals, said ratio signal being indicative of the type or average type of hydrocarbon gas, and display means responsive to said first absorbance signal and said ratio signal for providing an indication of the concentration and type of hydrocarbon gas in the gas sample.

14. A gas detecting apparatus according to claim 13, wherein said first wavelength is 3.2 microns, said second wavelength is 3.4 microns and said third wavelength is 3.9 microns.

15. A gas detecting apparatus according to claim 13, wherein said first wavelength is 3.2 microns, said second wavelength is 3.4 microns and said third wavelength is 2.9 microns.

16. A gas detecting apparatus according to claim 15, wherein said processing circuit means further comprises offset means for adjusting said ratio signal to be a preselected value when the ratio signal indicates that the type of hydrocarbon is methane.

17. A gas detecting apparatus according to claim 16, wherein said offset means includes means for producing an offset signal and circuit means for subtracting said offset signal from said first absorbance signal at the input of said ratio determining means.

18. A gas detecting apparatus according to claim 15, wherein said display means comprises first and second analog meters and third and fourth function generating circuit means, said third function generating circuit means being interposed between said ratio determining means and said second meter and responsive to said ratio signal for providing a signal corresponding to the logarithm of said ratio signal for driving said first meter or a first display, and said fourth function generating circuit means being interposed between said second function generating circuit means and said second meter and responsive to said second absorbance signal for providing a signal corresponding to the logarithm of said second absorbance signal for driving said second meter or a second display.

19. A gas detecting apparatus according to claim 18, wherein said second meter has a scale divided into a first reading portion to indicate the type of hydrocarbon is swamp gas; a second reading portion to indicate the type of hydrocarbon is natural gas; a third reading portion to indicate the type of hydrocarbon is ethane; a fourth reading portion to indicate the type of hydrocarbon is propane; and a fifth reading portion to indicate that the type of hydrocarbon is gasoline vapors.

* * * * *